(12) United States Patent
Shimada et al.

(10) Patent No.: US 9,448,240 B2
(45) Date of Patent: Sep. 20, 2016

(54) HYDROPHILIC THIOL PROBE

(75) Inventors: Takashi Shimada, Tsukuba (JP);
Taka-Aki Sato, Tokyo (JP); Koichi Tanaka, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 120 days.

(21) Appl. No.: 14/241,728

(22) PCT Filed: Aug. 17, 2012

(86) PCT No.: PCT/JP2012/070924
§ 371 (c)(1),
(2), (4) Date: Feb. 27, 2014

(87) PCT Pub. No.: WO2013/035513
PCT Pub. Date: Mar. 14, 2013

(65) Prior Publication Data
US 2014/0212980 A1    Jul. 31, 2014

(30) Foreign Application Priority Data
Sep. 9, 2011 (JP) ................. 2011-196958

(51) Int. Cl.
*G01N 33/68* (2006.01)
(52) U.S. Cl.
CPC .. *G01N 33/6848* (2013.01); *Y10T 436/145555* (2015.01); *Y10T 436/147777* (2015.01); *Y10T 436/173845* (2015.01); *Y10T 436/19* (2015.01); *Y10T 436/200833* (2015.01); *Y10T 436/24* (2015.01)
(58) Field of Classification Search
CPC ............. G01N 33/68; G01N 33/6803; G01N 33/6848; G01N 33/6851; Y10T 436/14; Y10T 436/145555; Y10T 436/147777; Y10T 436/17; Y10T 436/173845; Y10T 436/19; Y10T 436/20; Y10T 436/200833; Y10T 436/24
USPC ............. 436/86, 96, 98, 106, 111, 124, 126, 436/127, 128, 173; 250/281, 282; 544/194, 544/196; 560/226
See application file for complete search history.

(56) References Cited

U.S. PATENT DOCUMENTS

2010/0015717 A1\* 1/2010 Singh ................. G01N 33/6851
436/86
2011/0039277 A1\* 2/2011 Mastroberardino . G01N 33/542
435/7.1

FOREIGN PATENT DOCUMENTS

WO    WO-2006/025887 A2    3/2006
WO    WO-2011/018227 A2    2/2011

OTHER PUBLICATIONS

Supplementary European Search Report for the Application No. EP 12 83 0678 dated Nov. 24, 2014.
"EZ-Link Iodoacetyl-LC-Biotin; EZ-Link Iodoacetyl-PEG$_2$-Biotin", Thermoscientific, 2008, XP-002732349, pp. 1-4.
Hong, Fei et al., "Protein Synthesis, Post-Translation Modification, and Degradation: Specific Patterns of Electrophile Adduction Trigger Keap1 Ubiquitination and Nrf2 Activation", The Journal of Biological Chemistry, 2005, vol. 280, No. 36, pp. 31768-31775.
Written Opinion of the International Searching Authority (PCT/ISA/237) for Application No. PCT/JP2012/070924 mailed Oct. 2, 2012 (English translation mailed Mar. 20, 2014).
International Search Report for the Application No. PCT/JP2012/070924 mailed Oct. 2, 2012.
Kuyama, Hiroki et al., "A method for N-terminal *de novo* sequence analysis of proteins by matrix-assisted laser desorption/ionization mass spectrometry", Analytical Biochemistry, 2008, vol. 308, pp. 291-296.
Ross, Philip at al., "Multiplexed Protein Quantitation in *Saccharomyces cerevisiae* Using Amine-reactive Isobaric Tagging Reagents", Molecular & Cellular Proteomics, 2004, vol. 3, No. 12, pp. 1154-1169.
Shimbo, Kazutaka et al., "Precolumn derivatization reagents for high-speed analysis of amines and amino acids in biological fluid using liquid chromatography/electrospray ionization tandem mass spectrometry", Rapid Communications in Mass Spectrometry, 2009, vol. 23, pp. 1483-1492.
Masuda, Mayumi et al., "Fluorogenic Derivatization Reagents Suitable for Isolation and Identification of Cysteine-Containing Proteins Utilizing High-Performance Liquid Chromatography-Tandem Mass Spectrometry", Analytical Chemistry, 2004, vol. 76, No. 3, pp. 728-735.

(Continued)

*Primary Examiner* — Maureen Wallenhorst
(74) *Attorney, Agent, or Firm* — Cheng Law Group, PLLC

(57) ABSTRACT

A thiol probe for a protein, which promotes ionization in proteomic analysis using mass spectrometry and can be used even for a protein that has a high degree of hydrophobicity and quickly turns over, and is represented by the following formula (I):

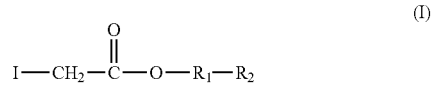

In formula (I), $R_1$ represents a linker group, and $R_2$ represents a substituted ammonium group or a substituted amino group. A mass spectrometry method for a protein, includes the steps of obtaining a modified protein by reacting the thiol probe with a protein to be subjected to mass spectrometry and subjecting the modified protein to mass spectrometry.

24 Claims, 5 Drawing Sheets

(56) References Cited

OTHER PUBLICATIONS

Kuyama, Hiroki et al., "An approach to quantitative proteome analysis by labeling tryptophan residues", Rapid Communications in Mass Spectrometry, 2003, vol. 17, pp. 1642-1650.

Wang, Dongxia et al., "Improved procedures for N-terminal sulfonation of peptides for matrix-assisted laser desorption/ionization post-source decay peptide sequencing", Rapid Communications in Mass Spectrometry, 2004, vol. 18, pp. 96-102.

Smolka, Marcus et al., "Optimization of the Isotope-Coded Affinity Tag-Labeling Procedure for Quantitative Proteome Analysis", Analytical Biochemistry, 2001, vol. 297, pp. 25-31.

Li, Jiaxu et al., "Protein Profiling with Cleavable Isotope-coded Affinity Tag (cICAT) Reagents", Molecular & Cellular Proteomics, 2003, vol. 2, No. 11, pp. 1198-1204.

Van Berkel, Gary et al., "Derivatization for Electrospray Ionization Mass Spectrometry. 3. Electrochemically Ionizable Derivatives", Analytical Chemistry, 1998, vol. 70, No. 8, pp. 1544-1554.

Iwahata, Daigo et al., "A highly sensitive analytical method for metal-labelled amino acids by HPLC/ICP-MS", Journal of Analytical Atomic Spectrometry, 2008, vol. 23, pp. 1063-1067.

Bonetto, Valentina et al., "C-Terminal Sequence Analysis of Peptides and Proteins Using Carboxypeptidases and Mass Spectrometry after Dervatization of Lys and Cys Residues", Analytical Chemistry, 1997, vol. 69, No. 7, pp. 1315-1319.

Ren, Diya et al., "Enrichment of Cysteine-Containing Peptides from Tryptic Digests Using a Quanternary Amine Tag", Analytical Chemistry, 2004, vol. 76, No. 15, pp. 4522-4530.

Takeda, Junpei et al., "MALDI-MS ni yoru Hanno Kassei Taishabutsu Screening o Shiko shita Teibunshi Probe no Kento", The Japan Society for Analytical Chemistry, 2010, vol. 59, Y1029, p. 339.

Shimada, Takashi et al., "Development of iodoacetic acid-based cysteine mass tags: Detection enhancement for cysteine-containing peptide by matrix-assisted laser desorption/ionization time-of-flight mass spectrometry", Analytical Biochemistry, 2012, vol. 421, pp. 785-787.

\* cited by examiner

| Probe ID | CC-02HI | CC-02Q | CC-03Q | CC-10HI | TOC-06 | TOC-07 | TOC-08 |
|---|---|---|---|---|---|---|---|
| Enhanced ratio | 18.5 | 121.1 | 222.5 | 167.7 | 13.4 | 66.6 | 53.3 |
| p-value | 3.59E-11 | 5.65E-12 | 3.22E-06 | 6.02E-10 | 4.21E-05 | 7.13E-09 | 0.029 |

| Probe ID | CC-02HI | CC-02Q | CC-03Q | CC-10HI | TOC-06 | TOC-07 | TOC-08 |
|---|---|---|---|---|---|---|---|
| Enhanced ratio | 1.4 | 16.6 | 16.5 | 11.1 | 2.4 | 5.3 | 37.7 |
| p-value | 0.010 | 5.08E-06 | 7.54E-06 | 1.94E-05 | 2.49E-03 | 3.86E-04 | 7.84E-05 |

HYDROPHILIC THIOL PROBE

TECHNICAL FIELD

The present invention belongs to the field of life science, especially proteomics, and relates to a mass spectrometry technique applicable to clinical diagnosis and the like. Specifically, the present invention relates to a reagent for mass spectrometry useful for LC/MS or MALDI-TOF MS. More specifically, the present invention relates to a novel hydrophilic thiol probe that improves the sensitivity of mass spectrometry of biomolecules.

BACKGROUND ART

In proteomics, there are many methodologies using, as an additional site for a probe, a thiol group of a cysteine residue of a protein or peptide. A probe whose additional site is a thiol group has also been commercialized as, for example, a labeling kit using biotin, a fluorescent indicator, alkaline phosphatase, or the like. Such a probe can be utilized also in biochemical assays (e.g., western blotting, ELISA, intracellular fluorescent labeling) or HPLC of proteins or peptides.

Further, in proteomics, there is also a methodology in which a protein or peptide is derivatized using a probe that can label a specific amino acid residue to analyze the protein or peptide with high sensitivity. Applying to the technique of mass spectrometry, probe addition to a specific amino acid residue, is a methodology essential for enhancing ionization in mass spectrometry and reliably improving analytical accuracy.

For example, an N-terminal amino group or an amino group of a lysine residue is utilized as an additional site for a probe. There is a methodology in which, as such a probe, for example, TMPP reagent (Anal. Biochem. 2008, 380(2), 291-296 (Non-Patent Document 1)), SPITC reagent (RCM. 2004, 18(1), 96-102 (Non-Patent Document 2)), or the like is used to make it possible to select the MS/MS ion series of a peptide.

Further, a revolutionary method for quantitative analysis has been developed in which labeling using a stable isotope reagent, ICAT (Isotope-Coated Affinity Tag) is performed when an alkyl group is introduced into a thiol group of a protein or peptide (Anal. Biochem. 2001, 297, 25-31 (Non-Patent Document 3)), and the reagent has also been modified as cleavable ICAT (Mol Cell Proteomics. 2003, 2, 1198-1204 (Non-Patent Document 4)).

Further, a method for simultaneous quantitation of proteins has also been modified as iTRAQ® (Isobaric tag for relative and absolute quantitation) (Mol Cell Proteomics. 2004, 3, 1154-1169 (Non-Patent Document 5)) to analyze changes in protein or peptide expression by mass spectrometry.

In addition to the above, methods for derivatizing proteins or peptides with various probes in mass spectrometry have been reported (Anal. Chem. 1998, 70, 1544-1554 (Non-patent Document 6), Rapid Commun. Mass Spectrom. 2009; 23: 1483-1492 (Non-Patent Document 7), J. Anal. At. Spectrom., 2008, 23, 1063-1067 (Non-Patent Document 8), Anal. Chem. 1997, 69, 1315-1319 (Non-Patent Document 9), and Anal. Chem. 2004, 76, 728-735 (Non-Patent Document 10)).

On the other hand, in proteomics, a reductive alkylation method is conventionally performed after denaturation of a protein as pretreatment for effective digestion of the protein so that reoxidation of cysteine residues is prevented. Specifically, a protein that has been subjected to, for example, electrophoretic separation or denaturation with a denaturing urea solution is reduced with dithiothreitol to generate thiol groups of cysteine residues. Then, the thiol groups are alkylated with iodoacetamide, iodoacetic acid, vinylpyridine, acrylamide, or the like to block reoxidation of the thiol groups. It is understood that derivatization of cysteine residues by such a method makes it easy to unfold the chain of a protein, and as a result, enzymatic digestion as a next step easily occurs and the efficiency of the digestion is increased.

PRIOR ART DOCUMENT

Non-Patent Documents

Non-Patent Document 1: Analytical Biochemistry, 2008, Vol. 380, No. 2, pp. 291-296
Non-Patent Document 2: Rapid Communications in Mass Spectrometry, 2004, Vol. 18, No. 1, pp. 96-102
Non-Patent Document 3: Analytical Biochemistry, 2001, Vol. 297, pp. 25-31
Non-Patent Document 4: Molecular & Cellular Proteomics, 2003, Vol. 2, pp. 1198-1204
Non-Patent Document 5: Molecular & Cellular Proteomics, 2004, Vol. 3, pp. 1154-1169
Non-Patent Document 6: Analytical Chemistry, 1998, Vol. 70, pp. 1544-1554
Non-Patent Document 7: Rapid Communications in Mass Spectrometry, 2009, Vol. 23, pp. 1483-1492
Non-Patent Document 8: Journal of Analytical Atomic Spectrometry, 2008, Vol. 23, pp. 1063-1067
Non-Patent Document 9: Analytical Chemistry, 1997, Vol. 69, pp. 1315-1319
Non-Patent Document 10: Analytical Chemistry, 2004, Vol. 76, pp. 728-735

SUMMARY OF THE INVENTION

Problems to be Solved by the Invention

However, the above-described reductive alkylation method has been performed only for the purpose of preventing reoxidation of cysteine, and has not been used for other purposes.

On the other hand, use of a probe that promotes peptide ionization makes it possible to detect a peptide having low sensitivity, but such a probe that promotes ionization has been conventionally used for a digested peptide of a protein to be identified. Such a digested peptide is characteristic in that its C-terminal inevitably has a basic amino acid such as lysine or arginine. It is empirically understood that such a characteristic sequence achieves high sensitivity in mass spectrometry.

However, biologically- or clinically-important proteins or peptides are not digested peptides but functional peptides typified by hormones, amyloids, cytokines, and the like. Such functional peptides do not always have a characteristic sequence that enzymatically-digested peptides have. Further, many of the functional peptides are difficult to be detected even by using a conventional probe due to their high hydrophobicity or quick turnover. Therefore, it is required to achieve favorable detection sensitivity and obtain meaningful results even when such functional proteins are analyzed by mass spectrometry.

Therefore, an object of the present invention is to provide a probe that further promotes ionization in proteomic analysis using mass spectrometry, and a high-sensitive mass spectrometry method for a protein using such a probe.

Another object of the present invention is to provide an ionization-enhancing probe that can be used even for a protein that has a high degree of hydrophobicity and quickly turns over, and a high-sensitive mass spectrometry method for a protein using such a probe.

Means for Solving the Problems

The present inventors have found that the above objects of the present invention are achieved by a probe that is molecularly designed so as to have a structure that can be introduced into a thiol group and a structure that promotes ionization, which has led to the completion of the present invention.

The present invention includes the followings.
(1) A thiol probe for a protein, which is represented by the following formula (I):

[Chemical Formula 1]

$$I-CH_2-\overset{O}{\underset{\|}{C}}-O-R_1-R_2 \quad (I)$$

wherein $R_1$ represents a linker group (i.e., a bivalent linker group), and $R_2$ represents a substituted ammonium group or a substituted amino group.

In the present invention, the term "protein" broadly refers to an amino acid polymer, and the amino acid polymer is not limited by the number of amino acids polymerized. Therefore, the term "protein" used herein includes all oligopeptides, polypeptides, and proteins.
(2) The thiol probe for a protein according to (1), wherein the linker group is a hydrocarbon group having 1 to 3 carbon atoms or an alkylene oxide-containing group having 2 to 6 carbon atoms.
(3) The thiol probe for a protein according to (2), wherein an alkylene oxide in the alkylene oxide-containing group is ethylene oxide or propylene oxide.
(4) The thiol probe for a protein according to any one of (1) to (3), wherein the substituted amino group is a group represented by $-NHR_3$, wherein $R_3$ represents a hydrocarbon group or a nitrogen-containing group.
(5) The thiol probe for a protein according to (4), wherein $R_3$ is an amidino group which may be substituted, or a triazino group which may be substituted.
(6) The thiol probe for a protein according to (5), wherein a substituent group in the triazino group which may be substituted is selected from the group consisting of an amino group and an alkoxy group having 1 or 2 carbon atoms.
(7) The thiol probe for a protein according to (5), wherein a substituent group in the amidino group which may be substituted is an alkyl group having 1 or 2 carbon atoms.
(8) The thiol probe for a protein according to any one of (1) and (2), wherein the substituted ammonium group is a tertiary or quaternary ammonium group substituted by an alkyl group having 1 or 2 carbon atoms.
(9) The thiol probe for a protein according to (8), which is represented by the following formula (i):

[Chemical Formula 2]

(i)

(10) The thiol probe for a protein according to (8), which is represented by the following formula (ii):

[Chemical Formula 3]

(ii)

(11) The thiol probe for a protein according to (8), which is represented by the following formula (iii):

[Chemical Formula 4]

(iii)

(12) The thiol probe for a protein according to (5), which is represented by the following formula (iv):

[Chemical Formula 5]

(iv)

(13) The thiol probe for a protein according to (5), which is represented by the following formula (v):

[Chemical Formula 6]

(v)

(14) The thiol probe for a protein according to (6), which is represented by the following formula (vi):

[Chemical Formula 7]

(vi)

(15) The thiol probe for a protein according to (6), which is represented by the following formula (vii):

[Chemical Formula 8]

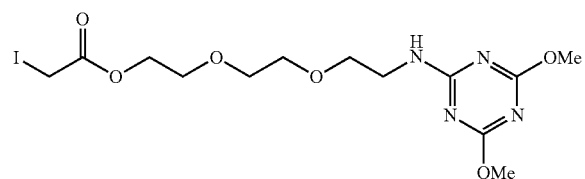

(vii)

(16) A mass spectrometry method for a protein, comprising the steps of:
obtaining a modified protein by reacting the thiol probe according to any one of (1) to (15) with a protein; and
subjecting the modified protein to mass spectrometry.

In (16), the protein to be reacted with the thiol probe may be a protein having a thiol group generated by reduction treatment.

Effects of the Invention

According to the present invention, it is possible to provide a probe that further promotes ionization in mass spectrometry, and a high-sensitive mass spectrometry method for a protein. According to the present invention, it is also possible to provide an ionization-enhancing probe that can be used even for a protein that has a high degree of hydrophobicity and quickly turns over, and a high-sensitive mass spectrometry method for a protein using such a probe.

Specifically, according to the present invention, it is possible to achieve about 2-fold to 200-fold improvement in sensitivity as compared to when only a reductive alkylation step using iodoacetamide, which is used in conventional proteomics to prevent oxidation of thiol groups, is performed.

Further, unlike a conventional probe having a high degree of hydrophobicity such as ICAT reagent, the probe according to the present invention is molecularly designed so as to reduce the degree of hydrophobicity of the whole molecule, and therefore a protein modified with the probe according to the present invention is more hydrophilic than before modification. Therefore, the probe according to the present invention can be used for a protein having a high degree of hydrophobicity. In addition to this, prevention of oxidation of thiol groups and treatment for enhancing ionization can be achieved at the same time by using, instead of an alkylation agent used in the conventional reductive alkylation step, the probe molecularly designed from the viewpoint of enhancing ionization and improving sensitivity, and a conventional protocol does not need to be changed. Further, the probe according to the present invention can be applied also to a low-abundance peptide that quickly turns over or a hydrophobic protein.

MODES FOR CARRYING OUT THE INVENTION

Figure 1:
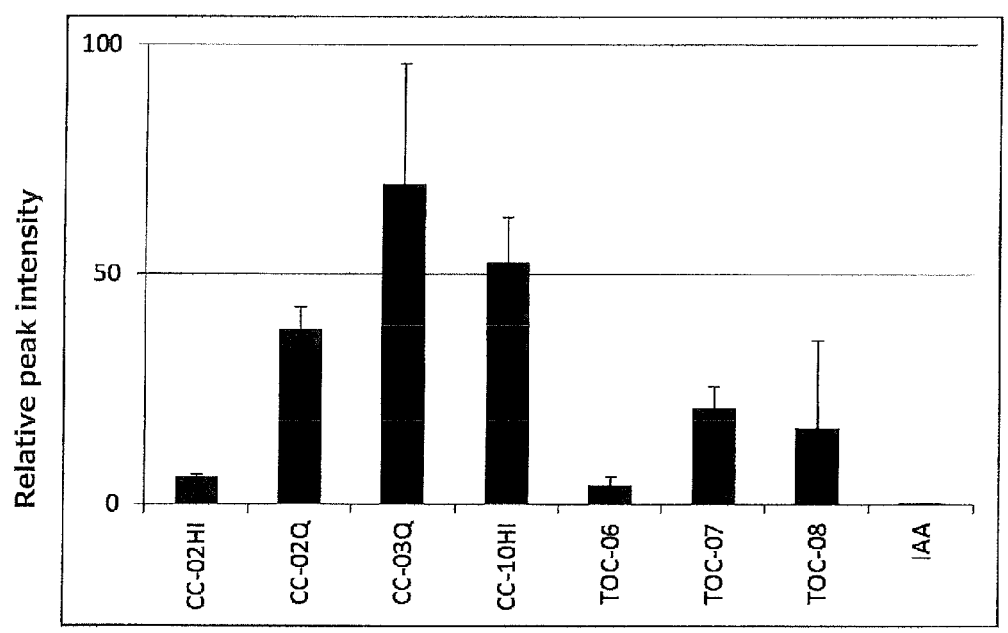
FIG. 1 is a graph showing the relative intensities of peaks of an alpha chain detected by mass spectrometry of Insulin samples with addition of each of thiol probes according to the present invention in comparison with a control (peptide with addition of IAA); and a table showing both a ratio relative to the control (Enhanced ratio) and a p-value obtained by statistically evaluating the degree of ionization promotion.

A thiol probe according to the present invention has characteristics such that the thiol probe has a structure having reactivity to a thiol group, a structure for reducing the degree of hydrophobicity of the whole molecule, and a structure that is easily protonated, and has no amide group that is a structure complicating a mass spectrum due to the cleavage of a probe itself in multi-stage mass spectrometry.

Specifically, the structure having reactivity to a thiol group is an iodoacetyl group that minimizes a side reaction to a functional group other than a thiol group (e.g., an amino group) and has high reaction rate selectivity.

The structure for reducing the degree of hydrophobicity of the whole molecule is an oxygen-containing group.

The structure that is easily protonated is a nitrogen-containing group.

More specifically, the thiol probe according to the present invention is represented by the following formula (I), that is, a structural formula having an iodoacetyl group ($ICH_2CO-$), an oxygen-containing group ($-OR_1-$), and a nitrogen-containing group ($-R_2$).

[Chemical Formula 9]

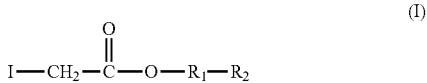

(I)

In the formula (I), $R_1$ represents a linker group. The linker group is, i.e., a bivalent linking group, and is usually a bivalent organic group.

The bivalent organic group may be a hydrocarbon group having 1 or 2 carbon atoms. If the number of carbon atoms exceeds the above range, the degree of hydrophobicity of the whole molecule becomes high, which tends to make it difficult to sufficiently obtain the effect of enhancing ionization.

Alternatively, the bivalent organic group may be an alkylene oxide-containing group having 2 to 6 carbon atoms. The alkylene oxide-containing group is preferably a polyalkylene oxide-containing group. More specifically, an alkylene oxide in the alkylene oxide-containing group is ethylene oxide or propylene oxide.

For example, the group represented by $OR_1$ is preferably a polyalkylene glycol group. The polyalkylene glycol group may be a group formed by the polymerization of an alkylene glycol having 2 to 6 carbon atoms. In the present invention, the polyalkylene glycol group may be selected from the group consisting of a polyethylene glycol group (a group formed by the polymerization of ethylene glycol) and a polypropylene glycol group (a group formed by the polymerization of 1,2-propanediol or 1,3-propanediol). It is to be noted that the degree of polymerization of glycol in the polyalkylene glycol group may be 2 to 6.

In the formula (I), $R_2$ represents a nitrogen-containing group. The nitrogen-containing group is a proton acceptor group, and is specifically a substituted ammonium group or a substituted amino group.

The substituted ammonium group may be a tertiary ammonium group or a quaternary ammonium group. A substituent group in the substituted ammonium group may be an alkyl group having 1 or 2 carbon atoms, or the like. The counter anion of the substituted ammonium group shall be a monovalent halogen anion. For example, the monovalent halogen anion may be $Cl^-$, $Br^-$, $I^-$, or the like.

The substituted amino group may be a group represented by —$NHR_3$.

In the group represented by —$NHR_3$, $R_3$ may be a hydrocarbon group having 1 or 2 carbon atoms or a nitrogen-containing group.

Preferably, $R_3$ may be an optionally substituted amidino group or an optionally substituted triazino group.

When $R_3$ is an optionally substituted amidino group, i.e., the group represented by —$NHR_3$ is an optionally substituted guanidino group. A substituent group in the optionally substituted amidino group may be an alkyl group having 1 or 2 carbon atoms, or the like.

A substituent group in the optionally substituted triazino group may be selected from the group consisting of an amino group and an alkoxy group having 1 or 2 carbon atoms.

The probe according to the present invention is hydrophilic as the whole molecule, and is soluble in water, methanol, and ethanol. Specifically, the probe is preferably soluble in the above solvents at room temperature (e.g., 20° C.±10° C.) at a concentration of 10 mM to 500 mM, 20 mM to 500 mM, or 10 mM to 100 mM.

More specific examples of the probe are represented by the following formulas (i), (ii), (iii), (iv), (v), (vii), and (vii).

[Chemical Formula 10]

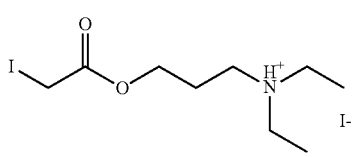

(i)

[Chemical Formula 11]

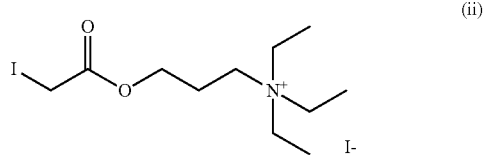

(ii)

[Chemical Formula 12]

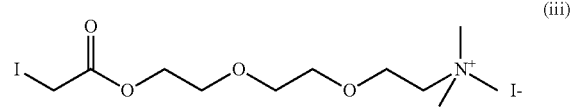

(iii)

[Chemical Formula 13]

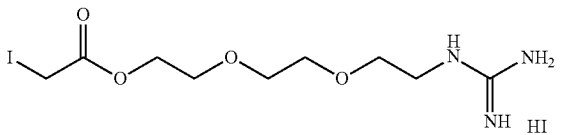

(iv)

[Chemical Formula 14]

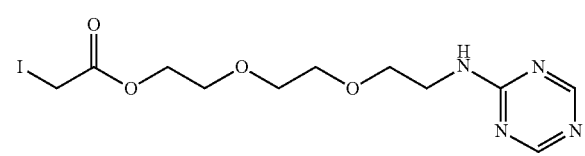

(v)

[Chemical Formula 15]

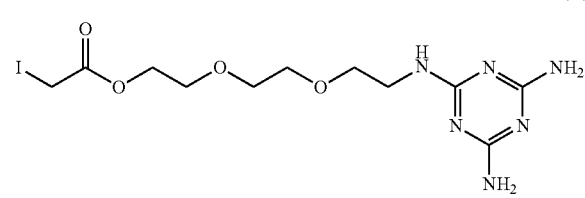

(vi)

[Chemical Formula 16]

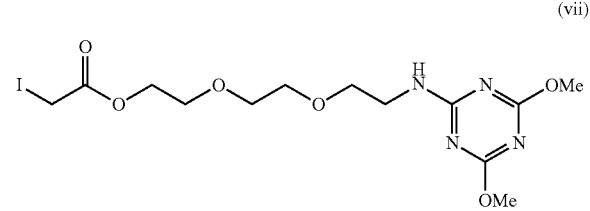

(vii)

A protein as an object to which the thiol probe is added is not particularly limited. The protein as an object to which the thiol probe is added broadly refers to an amino acid polymer, and the amino acid polymer is not limited by the number of amino acids polymerized, and therefore the range of molecular weight of the amino acid polymer is not particularly limited. Particularly, in the present invention, the protein is preferably a functional protein. The functional protein is a protein having a specific bioactivity, and examples thereof include hormones, amyloids, cytokines, and the like. The present invention is useful also when the protein as an object to which the thiol probe is added is a protein that has not been subjected to a fragmentation process such as digestion. Further, the effect of the present invention tends to be easily obtained when the molecular weight of the protein is large to some extent or when the protein contains a larger number of cysteine residues. The molecular weight of the object to which the thiol probe is added may usually be in the range of 1 kDa or larger, but may be in the range of, for example, 1.4 kDa or larger, 2 kDa or larger, 2.4 kDa or larger, or 3 kDa or larger. The upper limit of the above range is not particularly limited, but is, for example, 150 kDa.

The protein as an object to which the thiol probe is added naturally has a thiol group. The thiol group in the protein is usually derived from a cysteine residue. The thiol group is often oxidized to be a sulfino group (—$SO_2H$) or a salt thereof, a sulfo group (—$SO_3H$) or a salt thereof, a disulfide group (—SS—), or the like, and therefore reduction treatment is usually performed to generate a thiol group before the thiol probe is introduced.

Hereinbelow, the process of modifying a protein with the thiol probe according to the present invention will be illustrated.

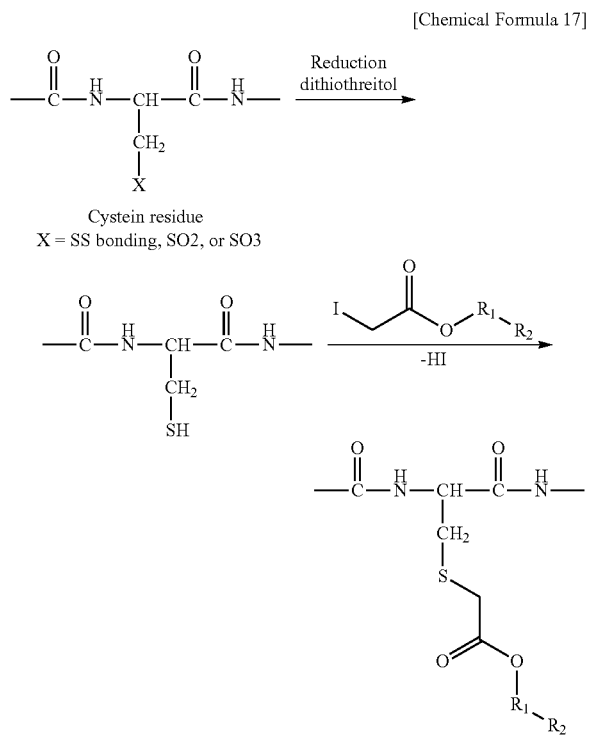

[Chemical Formula 17]

In a cysteine residue, as shown by X in the above formula, a disulfide group (SS bonding), an $SO_2^-$ group, or an $SO_3^-$ group may be generated. Such a cysteine residue is subjected to, for example, reduction with a reducing agent such as dithiothreitol to generate a thiol group (—SH group), and further the thiol probe ($ICH_2CO_2R_1R_2$) according to the present invention is attached to the thiol group. In this way, a probe-modified protein can be obtained.

The specific protocol of the above process of reduction and modification with the thiol probe can be easily determined by those skilled in the art in accordance with conventional reductive alkylation. That is, the same protocol as the conventional reductive alkylation can be used except that the thiol probe according to the present invention is used instead of iodoacetamide used in an alkylation process in the conventional method. Specifically, a reaction can be performed using the probe at a concentration of 20 mM to 50 mM at room temperature (e.g., 20° C.±10° C.) for 30 minutes to 60 minutes.

The protein modified with the thiol probe according to the present invention is subjected to mass spectrometry. Examples of an ion source of a device used in mass spectrometry include an electrospray ion source, a matrix-assisted laser desorption/ionization ion source, and the like. As an analyzer, a magnetic deflection-type analyzer, a quadrupole-type analyzer, an ion trap-type analyzer, a time of flight-type analyzer, a Fourier transform ion cyclotron resonance-type analyzer, or the like can be appropriately combined.

When a matrix-assisted laser desorption/ionization ion source is used as the ion source, a conventionally-used matrix for a protein, such as α-cyano-4-hydroxycinnamic acid, sinapic acid, or 2,5-dihydroxybenzoic acid, can be used as a matrix.

Further, a tandem mass spectrometer that can perform multi-stage $MS^n$ (n is 2 or more) mass spectrometry is preferably used.

The thiol probe according to the present invention has the effect of enhancing ionization and is therefore excellent in quantitative property. Therefore, the thiol probe according to the present invention can be also used as a quantification reagent that is a combination of a molecule having a predetermined structure (unlabeled probe) and a molecule having a structure in which some of the constituent atoms of the above molecule are replaced with stable isotopes (stable isotope-labeled probe). Such a quantification reagent can be used for differential analysis.

Specifically, (1) two protein samples different in state, e.g., protein samples in two different states of a protein sample I to be analyzed and a control protein sample II are prepared, (2) the protein sample I is modified with any one of the unlabeled probe and the stable isotope-labeled probe, and the protein sample II is separately modified with the other of the unlabeled probe and the stable isotope-labeled probe, (3) the modified protein sample I and the modified protein sample II are mixed with each other, and (4) the thus obtained modified protein mixture can be subjected to mass spectrometry without being subjected to a digestion process.

EXAMPLES

Hereinbelow, the present invention will be specifically described with reference to an example, but is not limited to the following example.

Example 1

1. The following samples (protein or peptides), reagents, and device were prepared.
One protein widely used as a model for reductive alkylation of protein;
  Insulin (Sigma-Aldrich) in which an alpha chain and a beta chain are linked via SS bonds of cysteine:
    alpha chain: GIVEQC CASVCSLYQL ENYCN (SEQ ID NO: 1)
    beta chain: FVNQHL CGSHLVEALY LVCGERGFFY TPKA (SEQ ID NO: 2)
Three models of a peptide containing only one cysteine;
  NC4 CLAC-P (Anaspec)
  LGPDGLPMPG CWQK (SEQ ID NO: 3)
  PSA2 (Anaspec)
  KLQCVDLHV (SEQ ID NO: 4)
  S26C Amyloid-beta (17-40) (Anaspec)
  LVFFAEDVGC NKGAIIGLMV GGVV (SEQ ID NO: 5)
One internal standard peptide;
  P14R (Sigma-Aldrich)
  PPPPPPPPPP PPPPR (SEQ ID NO: 6)
Other general-purpose reagents;
  ammonium bicarbonate (Fluka)
  dithiothreitol (Wako Pure Chemical Industries, Ltd.)
  iodoacetamide (Wako Pure Chemical Industries, Ltd.)
  α-cyano-4-hydroxycinnamic acid (CHCA) (SHIMADZU GLC Ltd.)

trifluoroacetic acid (Wako Pure Chemical Industries, Ltd.)
acetonitrile (Wako Pure Chemical Industries, Ltd.)
ZipTip C18 (Millipore)
Use device;
AXIMA® Performance (SHIMADZU CORPORATION)
2. The following thiol probes were prepared. The compound ID (compound id), proton acceptor group (group), molecular formula (formula), molecular weight (MW), molecular weight shift by binding to the peptide; delta mass (dM), and structure (structure) of each of the prepared thiol probes are shown below.

2. Each of the protein and peptide samples was treated in the following manner. It is to be noted that amounts expressed as % are based on volume.

The peptide was dissolved in an aqueous solution containing 0.05% TFA and 50% acetonitrile, and 200-pmol (100 pmol/μL, 2 μL) aliquots were dispensed.

Ten microliters (10 μL) of an aqueous solution containing 100 mM $NH_4HCO_3$ and 10 mM Dithiothreitol was added, and pH was confirmed (the pH was about 8.3).

Incubation was performed at 56° C. for 30 minutes.

TABLE 1

| compound id | group | formula | MW | dM | structure |
|---|---|---|---|---|---|
| CC-02 HI | DEAE | C9H19I2NO2 | 427.06 | 171.24 | 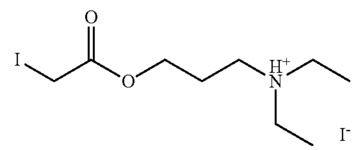 |
| CC-02 Q | Quaternary-amine | C11H23I2NO2 | 455.11 | 200.30 | 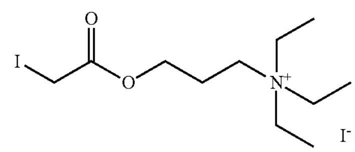 |
| CC-03 Q | Quaternary-amine | C11H23I2NO4 | 487.11 | 232.30 | 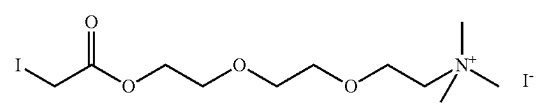 [SMILES: C[N+](C)(C)CCOCCOCCOC(=O)CI ; [I-]] |
| CC-10 HI | Gaunidine | C9H19I2N3O4 | 487.07 | 231.25 | 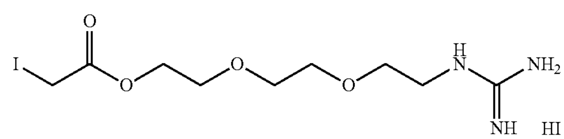 |
| TOC-06 | Triazine | C11H17IN4O4 | 396.18 | 268.27 | 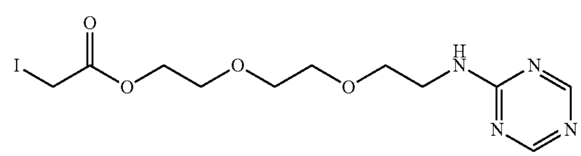 [SMILES: O=C(CI)OCCOCCOCCNc1ncncn1] |
| TOC-07 | Triazine | C11H19IN6O4 | 426.21 | 298.30 | 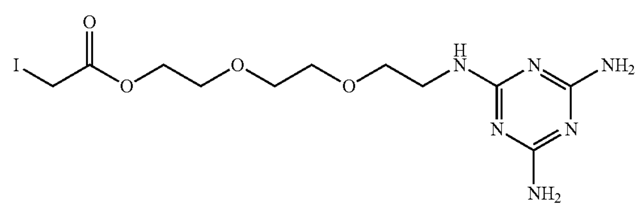 [SMILES: Nc1nc(N)nc(NCCOCCOCCOC(=O)CI)n1] |
| TOC-08 | Triazine | C13H21IN4O6 | 456.23 | 328.32 | 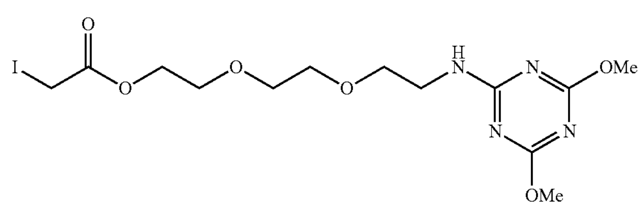 [SMILES: COc1nc(NCCOCCOCCOC(=O)CI)nc(OC)n1] |
| IAA | control | C2H4INO | 184.96 | 57.05 | 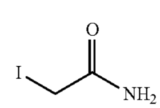 |

Fifteen microliters (15 μL) of a 50 mM probe solution was added, and the mixture was stirred at room temperature for 30 minutes in a dark place. The solvent of the probe solution was as follows:

water in the case of CC-02 HI, CC-02 Q, CC-03 Q, CC-10 HI, and IAA and;

methanol in the case of TOC-06, TOC-07, and TOC-08.

Five microliters (5 μL) of a 10% aqueous TFA solution was added to terminate reaction.

Two microliters (2 μL) of the reaction solution was diluted with the following amount of a 0.1% aqueous TFA solution, and then purified by desalting using ZipTip C18:

twenty microliters (20 μL) of an aqueous TFA solution in the case of CC-02 HI, CC-02 Q, CC-03 Q, CC-10 HI, and IAA and;

two hundred microliters (200 μL) of an aqueous TFA solution in the case of TOC-06, TOC-07, and TOC-08.

3. MS analysis was performed under the following conditions. It is to be noted that amounts expressed as % are based on volume.

For each of the probes, 12 samples to be subjected to MS were prepared.

As an internal standard, 0.3 pmol of P14R was added.

As a matrix, 1 μL of a solution in which 5 mg/ml of CHCA was dissolved in an aqueous solution containing 0.1% TFA and 50% acetonitrile was added per well.

Mass spectrometry was performed by automatic measurement using raster scanning (300 profile/run).

The measurement was performed in linear positive mode.

4. Data analysis was performed in the following manner.

A peak in which mass number shift was caused by probe addition was defined as a target peak, and the intensity of the target peak was corrected for the peak intensity of the internal standard P14R.

The first and second highest values and the first and second lowest values were eliminated as abnormal values (35% trim-mean). It is empirically known that in MALDI MS analysis, a hot spot where an ion is very easily generated is present, and on the other hand, a spot where an ion is hardly generated is present depending on the spot irradiated with laser light. Therefore, it is necessary to determine how to analyze MALDI MS data on the assumption that abnormal values are always present.

The variation of data (SD value) was determined and the degree of ionization promotion was statistically evaluated (p-value).

Figure 2:
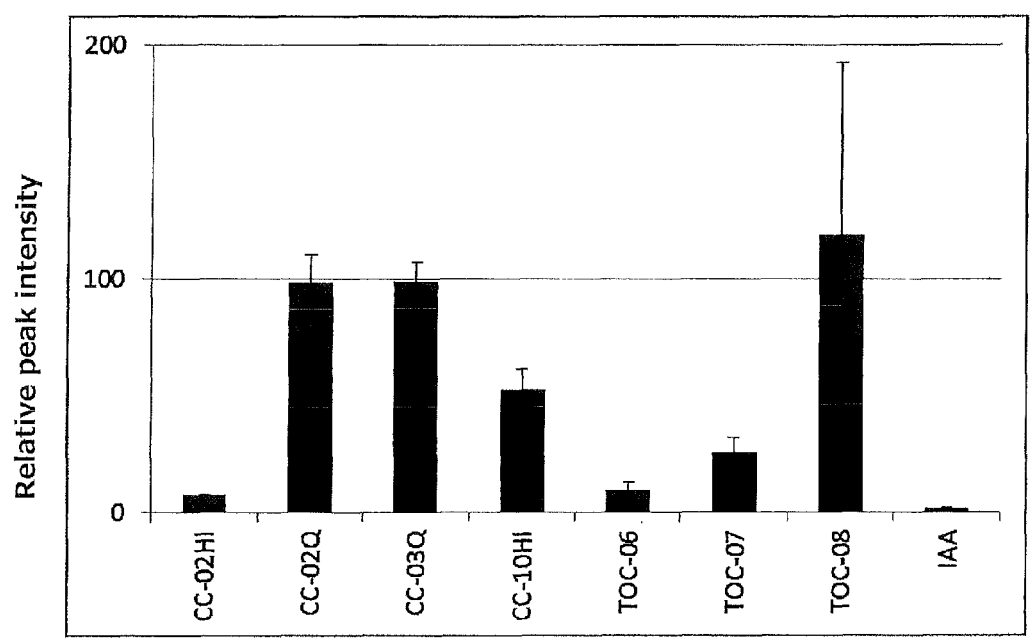
FIG. 2 is a graph showing the relative intensities of peaks of a beta chain detected by mass spectrometry of Insulin samples with addition of each of thiol probes according to the present invention in comparison with a control (peptide with addition of IAA); and a table showing both a ratio relative to the control (Enhanced ratio) and a p-value obtained by statistically evaluating the degree of ionization promotion.
Figure 3:
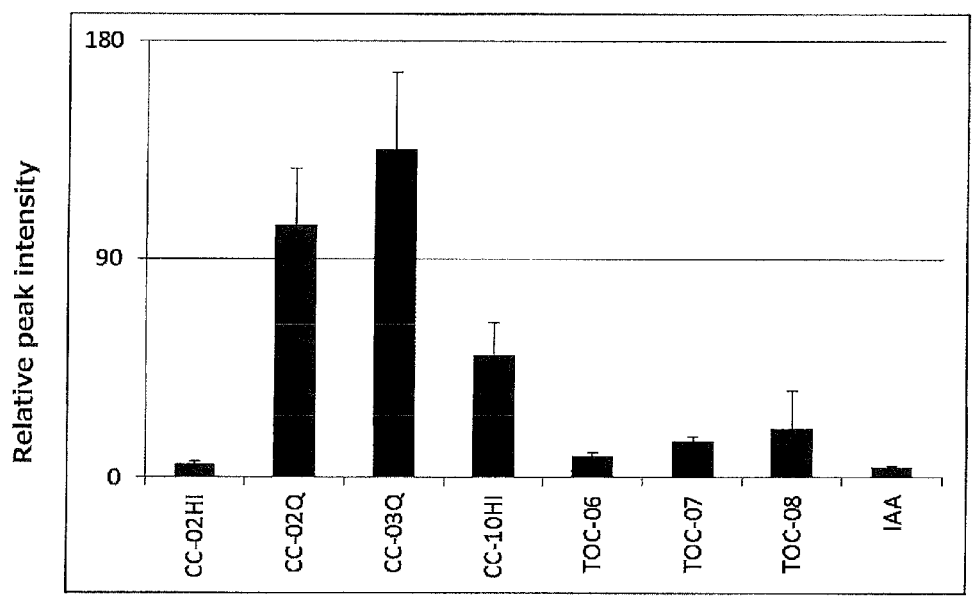
FIG. 3 is a graph showing the relative intensities of peaks detected by mass spectrometry of NC4 CLAC-P samples with addition of each of thiol probes according to the present invention in comparison with a control (peptide with addition of IAA); and a table showing both a ratio relative to the control (Enhanced ratio) and a p-value obtained by statistically evaluating the degree of ionization promotion.
Figure 4:
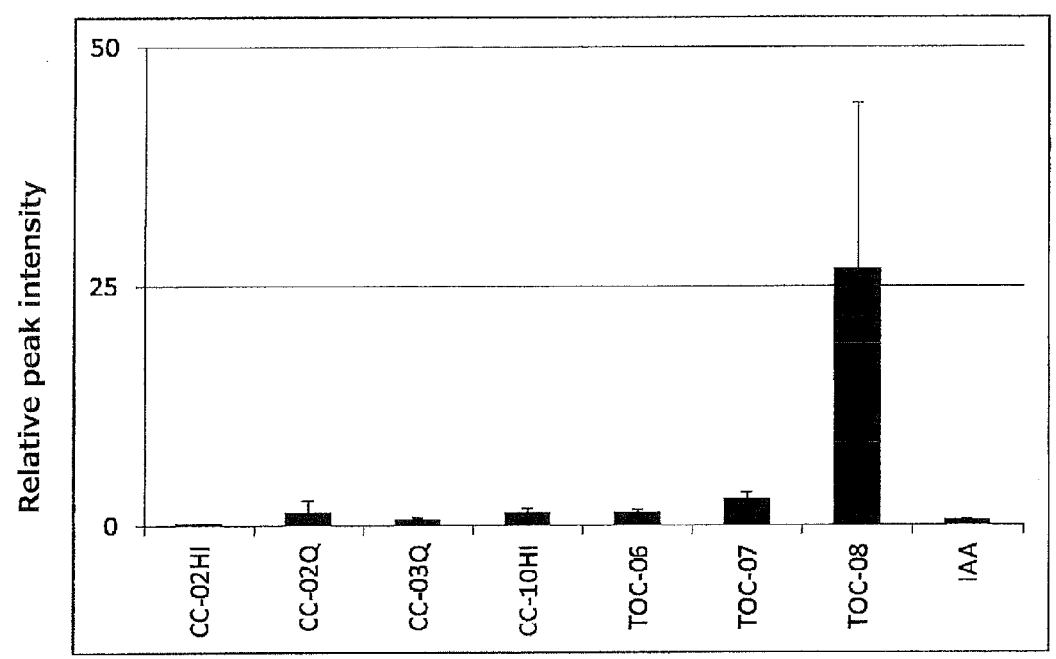
FIG. 4 is a graph showing the relative intensities of peaks detected by mass spectrometry of PSA2 samples with addition of each of thiol probes according to the present invention in comparison with a control (peptide with addition of IAA); and a table showing both a ratio relative to the control (Enhanced ratio) and a p-value obtained by statistically evaluating the degree of ionization promotion.
Figure 5:
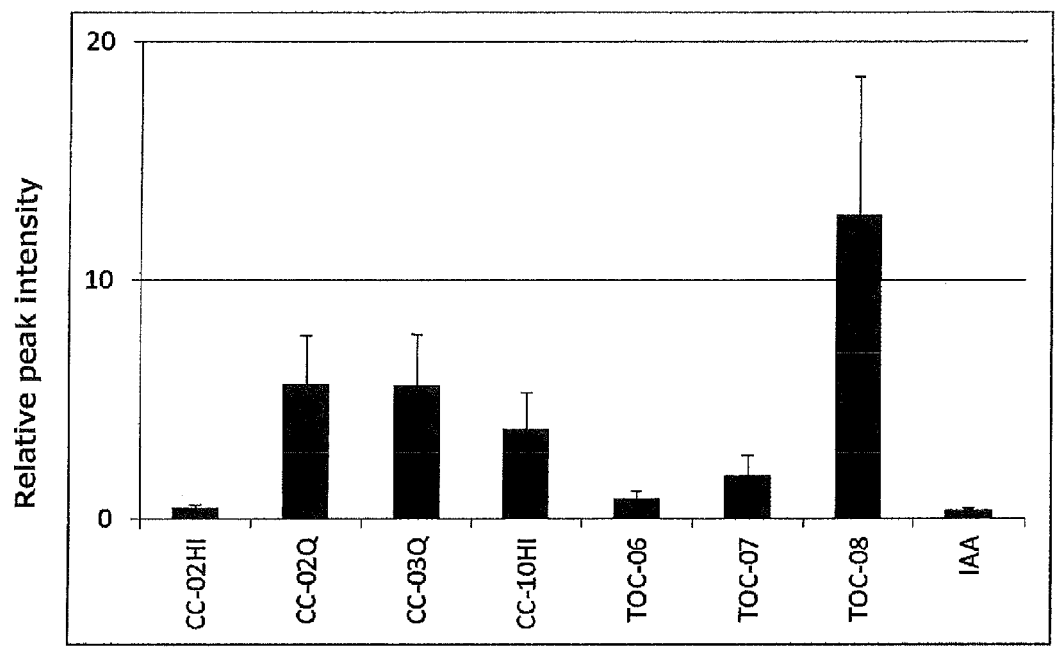
FIG. 5 is a graph showing the relative intensities of peaks detected by mass spectrometry of S26C Amyloid-beta samples with addition of each of thiol probes according to the present invention in comparison with a control (peptide with addition of IAA); and a table showing both a ratio relative to the control (Enhanced ratio) and a p-value obtained by statistically evaluating the degree of ionization promotion.

The analysis results of the alpha chain of Insulin, the beta chain of Insulin, NC4 CLAC-P, PSA2, and S26C Amyloid-beta are shown in FIGS. 1 to 5, respectively. Each of FIGS. 1 to 5 is a graph showing the variation of relative peak intensities observed in each sample for each of the probes used, and a table showing a peak intensity ratio of each sample relative to the control (IAA) (Enhanced ratio) and a p-value determined by statistically evaluating the degree of ionization promotion (p-value). It is to be noted that in each of the tables, E refers to a power of 10, and a negative integer following E is the exponent to the base 10.

SEQUENCE LISTING FREE TEXT

SEQ ID NO: 6 is an artificial polypeptide.

The invention claimed is:

1. A thiol probe for a protein, which is represented by the following formula (I):

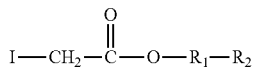

(I)

wherein $R_1$ represents a linker group which is either a hydrocarbon group having 1 to 3 carbon atoms or an alkylene oxide-containing group having 2 to 6 carbon atoms, and wherein an alkylene oxide in the alkylene oxide-containing group is ethylene oxide or propylene oxide, and wherein $R_2$ represents a substituted amino group represented by —$NHR_3$, wherein $R_3$ represents an amidino group which may be substituted, or a triazino group which may be substituted.

2. The thiol probe for a protein according to claim 1, wherein a substituent group in the triazino group which may be substituted is selected from the group consisting of an amino group and an alkoxy group having 1 or 2 carbon atoms.

3. The thiol probe for a protein according to claim 2, which is represented by the following formula (vi):

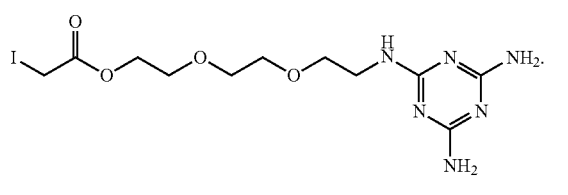

4. The thiol probe for a protein according to claim 2, which is represented by the following formula (vii):

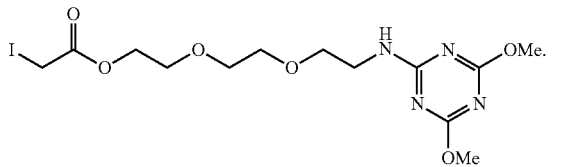

5. The thiol probe for a protein according to claim 1, wherein a substituent group in the amidino group which may be substituted is an alkyl group having 1 or 2 carbon atoms.

6. The thiol probe for a protein according to claim 1, which is represented by the following formula (iv):

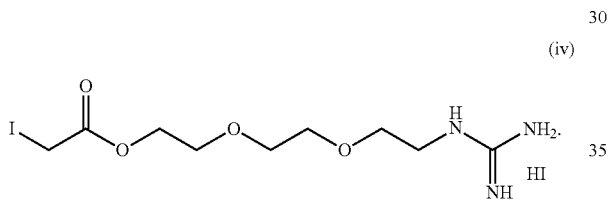

7. The thiol probe for a protein according to claim 1, which is represented by the following formula (v):

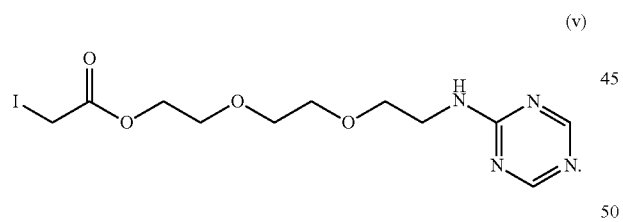

8. A thiol probe for a protein, which is represented by the following formula (I):

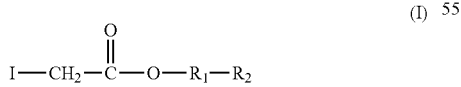

wherein $R_1$ represents a linker group which is either a hydrocarbon group having 1 to 3 carbon atoms or an alkylene oxide-containing group having 2 to 6 carbon atoms, and wherein an alkylene oxide in the alkylene oxide-containing group is ethylene oxide or propylene oxide, and wherein $R_2$ represents a substituted ammonium group, wherein the substituted ammonium group is a tertiary or quaternary ammonium group substituted by an alkyl group having 1 or 2 carbon atoms.

9. The thiol probe for a protein according to claim 8, which is represented by the following, formula (i):

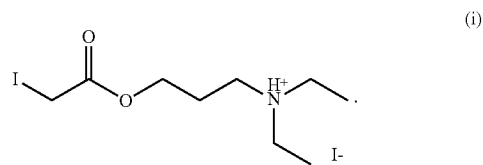

10. The thiol probe for a protein according to claim 8, which is represented by the following formula (ii):

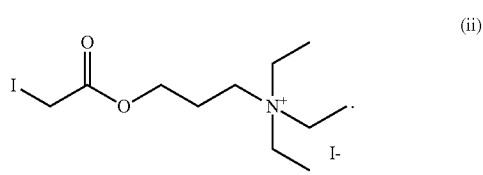

11. The thiol probe for a protein according to claim 8, which is represented by the following, formula (iii):

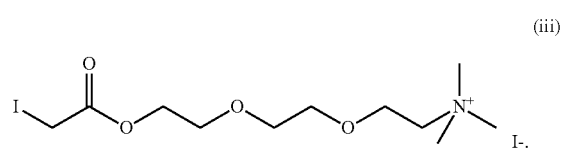

12. A mass spectrometry method for a protein, comprising the steps of:

obtaining a modified protein by reacting a thiol probe for a protein with a protein; and subjecting the modified protein to mass spectrometry, wherein the thiol probe for a protein is represented by the following formula (I):

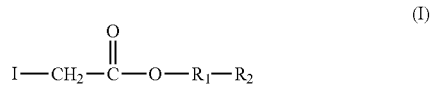

wherein $R_1$ represents a linker group, and $R_2$ represents a substituted ammonium group or a substituted amino group, wherein the linker group is an alkylene oxide-containing group having 2 to 6 carbon atoms, and wherein an alkylene oxide in the alkylene oxide-containing group is ethylene oxide or propylene oxide.

13. A mass spectrometry method for a protein, comprising the steps of:

obtaining a modified protein by reacting a thiol probe for a protein with a protein; and subjecting the modified protein to mass spectrometry, wherein the thiol probe for a protein is represented by the following formula (I):

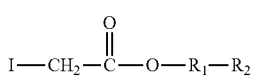

wherein R₁ represents a linker group, and R₂ represents a substituted amino group, and wherein the substituted amino group is a group represented by —NHR₃, wherein R₃ represents a hydrocarbon group or a nitrogen-containing group.

14. The mass spectrometry method for a protein according to claim 13, wherein R₃ is an amidino group which may be substituted, or a triazino group which may be substituted.

15. The mass spectrometry method for a protein according to claim 14, wherein a substituent group in the triazino group which may be substituted is selected from the group consisting of an amino group and an alkoxy group having 1 or 2 carbon atoms.

16. The mass spectrometry method for a protein according to claim 15, wherein the thiol probe is represented by the following formula (vi):

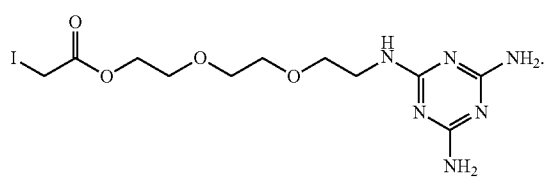

17. The mass spectrometry method for a protein according to claim 15, wherein the thiol probe is represented by the following formula (vii):

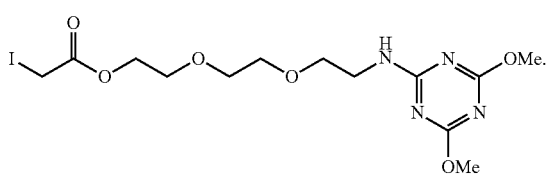

18. The mass spectrometry method for a protein according to claim 14, wherein a substituent group in the amidino group which may be substituted is an alkyl group having 1 or 2 carbon atoms.

19. The mass spectrometry method for a protein according to claim 14, wherein the thiol probe is represented by the following formula (iv):

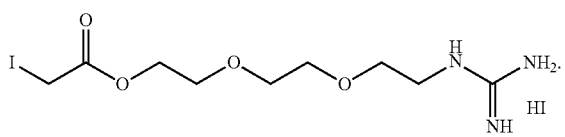

20. The mass spectrometry method for a protein according to claim 14, wherein the thiol probe is represented by the following formula (v):

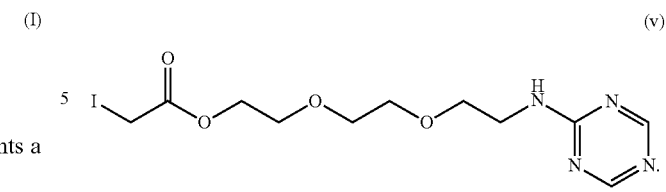

21. A mass spectrometry method for a protein, comprising the steps of:

obtaining a modified protein by reacting a thiol probe for a protein with a protein; and subjecting the modified protein to mass spectrometry, wherein the thiol probe for a protein is represented by the following formula (I):

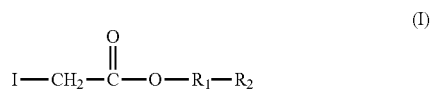

wherein R₁ represents a linker group, and R₂ represents a substituted ammonium group, and wherein the substituted ammonium group is a tertiary or quaternary ammonium group substituted by an alkyl group having 1 or 2 carbon atoms.

22. The mass spectrometry method for a protein according to claim 21, wherein the thiol probe is represented by the following formula (i):

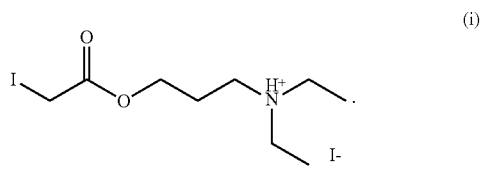

23. The mass spectrometry method for a protein according to claim 21, wherein the thiol probe is represented by the following formula (ii):

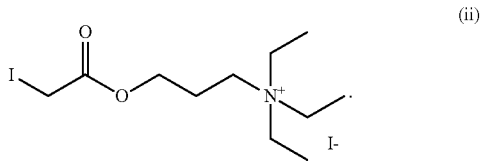

24. The mass spectrometry method for a protein according to claim 21, wherein the thiol probe is represented by the following formula (iii):

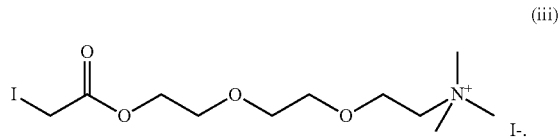

* * * * *

```
                               SEQUENCE LISTING

<160> NUMBER OF SEQ ID NOS: 6

<210> SEQ ID NO 1
           <211> LENGTH: 21
           <212> TYPE: PRT
           <213> ORGANISM: human
           <220> FEATURE:
           <221> NAME/KEY: DISULFID
           <222> LOCATION: (6)..(11)
           <220> FEATURE:
           <221> NAME/KEY: DISULFID
           <222> LOCATION: (7)..(7)
           <220> FEATURE:
           <221> NAME/KEY: DISULFID
           <222> LOCATION: (20)..(20)

<400> SEQUENCE: 1

Gly Ile Val Glu Gln Cys Cys Ala Ser Val Cys Ser Leu Tyr Gln Leu
           1               5                   10                  15

Glu Asn Tyr Cys Asn
                       20

<210> SEQ ID NO 2
           <211> LENGTH: 30
           <212> TYPE: PRT
           <213> ORGANISM: human
           <220> FEATURE:
           <221> NAME/KEY: DISULFID
           <222> LOCATION: (7)..(7)
           <220> FEATURE:
           <221> NAME/KEY: DISULFID
           <222> LOCATION: (19)..(19)
```

```
<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Ala
            20                  25                  30

<210> SEQ ID NO 3
<211> LENGTH: 18
<212> TYPE: PRT
<213> ORGANISM: human

<400> SEQUENCE: 3

His Met Ala Asn Leu Gly Pro Asp Gly Leu Pro Met Pro Gly Cys Trp
1               5                   10                  15

Gln Lys

<210> SEQ ID NO 4
<211> LENGTH: 9
<212> TYPE: PRT
<213> ORGANISM: human

<400> SEQUENCE: 4

Lys Leu Gln Cys Val Asp Leu His Val
1               5

<210> SEQ ID NO 5
<211> LENGTH: 29
<212> TYPE: PRT
<213> ORGANISM: human

<400> SEQUENCE: 5

His Met Ala Asn His Leu Val Phe Phe Ala Glu Asp Val Gly Cys Asn
1               5                   10                  15

Lys Gly Ala Ile Ile Gly Leu Met Val Gly Gly Val Val
            20                  25

<210> SEQ ID NO 6
<211> LENGTH: 15
<212> TYPE: PRT
<213> ORGANISM: artificial
<220> FEATURE:
<223> OTHER INFORMATION: synthetic polypeptide

<400> SEQUENCE: 6

Pro Pro Pro Pro Pro Pro Pro Pro Pro Pro Pro Pro Pro Pro Arg
1               5                   10                  15
```